Figure 1A:
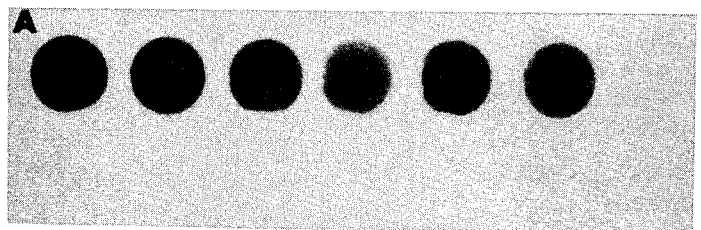

United States Patent [19]

Salyers et al.

[11] Patent Number: 4,977,251

[45] Date of Patent: Dec. 11, 1990

[54] DNA PROBES FOR IDENTIFICATION OF BACTEROIDES SPECIES

[75] Inventors: Abigail A. Salyers, Champaign, Ill.; Alex P. Kuritza, Los Angeles, Calif.

[73] Assignee: University of Illinois Board of Trustees, Urbana, Ill.

[21] Appl. No.: 236,305

[22] Filed: Aug. 23, 1988

Related U.S. Application Data

[63] Continuation of Ser. No. 8,904, Jan. 30, 1987, abandoned.

[51] Int. Cl.$^5$ .............................................. C07H 21/00
[52] U.S. Cl. ...................................... 536/27; 536/28; 536/29; 435/6
[58] Field of Search ............................... 536/27; 435/6

[56] References Cited

U.S. PATENT DOCUMENTS 4,652,517 3/1987 Scholl et al. ............................. 435/5

FOREIGN PATENT DOCUMENTS 0199439 3/1986 European Pat. Off. .

OTHER PUBLICATIONS

Kuritza et al., "DNA Probes for Identification of Clinically Important Bacteroides Species", American Society for Microbiology, (1986).

French et al., "DNA Probe Detection of Periodontal Pathogens", Oral Microbiol. Immunol., (1986).

Groves et al., "Preparation of ribonucleic acid Probes specific for Bacteroides fragilis", Diagn. Microbiol. Infect. Disc., (1987).

Primary Examiner—Ronald W. Griffin
Assistant Examiner—James O. Wilson
Attorney, Agent, or Firm—Marshall, O'Toole, Gerstein, Murray & Bicknell

[57] ABSTRACT

DNA hybridization probes have been developed which identify *Bacteroides fragilis*, members of the *Bacteroides fragilis* group of species, and members of *Bacteroides - Fusobacterium*. These probes can be used to detect these obligately anaerobic bacteria in clinical specimens.

5 Claims, 3 Drawing Sheets

DNA PROBES FOR IDENTIFICATION OF BACTEROIDES SPECIES

This application is a continuation application of application Ser. No. 008,904, filed Jan. 30, 1987, and now abandoned.

The invention herein described relates to novel DNA hybridization probes for certain *Bacteroides* and *Fusobacterium* species which are responsible for a variety of human clinical infections. These obligately anaerobic bacteria are difficult to cultivate and classify by means of conventional techniques.

By way of background, gram-negative anaerobic bacteria are recognized as pathogens of major importance and are capable of establishing infections in virtually any organ or tissue (Finegold, S. M. 1977. Anaerobic bacteria in human disease. Academic Press, Inc. New York). The anaerobes that are most frequently isolated from human clinical specimens are *Bacteroides* species [Finegold, S. M., supra; Finegold, S. M., and D. M. Citron. 1980. Gram-negative, nonsporeforming anaerobic bacilli, p. 431–439. In E. H. Lennette, A. Balows, W. J. Hausler, Jr., and J. P. Truant (ed.), Manual of clinical microbiology, 3rd ed. American Society for Microbiology, Washington, D.C.]. One species, *Bacteroides fragilis*, accounts for over half of these isolates [Allen, S.D., and J. A. Siders, 1980. Procedures for isolation and characterization of anaerobic bacteria, p. 397–417. In E. H. Lennette, A. Balows, W. J. Hausler, Jr., and J. P. Truant (ed.). Manual of clinical microbiology, 3rd ed. American Society for Microbiology, Washington, D.C., Finegold, S. M., supra; Finegold, S. M. et al., supra]. *B. fragilis* is a component of the resident flora of the human colon. Other human colonic *Bacteroides* species, such as *B. thetaiotaomicron*, *B. distasonis*, *B. ovatus*, *B. uniformis*, and *B. vulgatus*, are also frequently isolated from human clinical specimens. These species are often referred to collectively as the "*B. fragilis* group" because they behave similarly to *B. fragilis* on many biochemical tests. In some cases it is difficult to differentiate these species on the basis of biochemical tests [Allen, S.D. et al., supra; Holdeman, L. V., E. P. Cato, and W. E. C. Moore (ed.). 1977. Anaerobe laboratory manual, 4th ed. Virginia Polytechnic Institute and State University, Blacksburg]. Despite this, they are not closely related. Results of DNA-DNA hybridization studies indicate that they have cross-homologies with *B. fragilis* ranging from 14 to 28% (Johnson, J. L. 1978. Taxonomy of the *Bacteroides*. I. Deoxyribonucleic acid homologies among *Bacteroides fragilis* and other saccharolytic *Bacteroides* spp. Int. J. Syst. Bacteriol. 28:245–256). Other gram-negative anaerobes which are isolated from human clinical specimen include oral *Bacteroides* species (e.g., *B. melaninogenesis*, *B. asaccharolyticus*, and *B. oralis*) and *Fusobacterium*, a genus that is in the same phyllogenetic group as *Bacteroides* (Paster, B. J., W. Ludwig, W. G. Weisberg, E. Stackebrandt, R. B. Hespell, C. M. Hahn, H. Reichenbach, K. O. Stetter, and C. R. Woese. 1985. A phylogenetic grouping of the bacteroides, cytophages and certain flavobacteria. Syst. Appl. Microbiol. 6:34–42).

A combination of biochemical tests and gas-liquid chromatography is currently the most accurate method for identification of gram-negative anaerobes (Allen, S. D. et al., supra; Holdeman, I. V. et al., supra), but this method is time-consuming. Commercial kits for rapid identification of anaerobes, though less costly and more convenient, are less accurate and supplementary biochemical testing may be necessary (Applebaum, P. C., C. S. Kaufman, J. C. Keifer, and H. J. Venbrux. 1983. Comparison of three methods for anaerobe identification. J. Clin. Microbiol. 18:614–621; Buesching, W. J., J. R. Svirbely, and L. W. Ayers. 1983. Evaluation of the Anaerobe-Tek system for identification of anaerobic bacteria. J. Clin. Microbiol. 17:824–829). A more desirable method for identification of anaerobes would be a single accurate test such as a test based on specific DNA hybridization probes. Recent reports have described the use of DNA probes for detecting a variety of organisms, including Enterobacteriaceae (Fitts, R., M. Diamond, C. Hamilton, and M. Nevi. 1983. DNA-DNA hybridization assay for detection of *Salmonella* spp. in foods. Appl. Environ. Microbiol. 46:1146–1151; Hills, W. E., W. L. Payne, and C. C. G. Aulisio. 1983. Detection and enumeration of virulent *Yersinia enterocolitica* in food by DNA colony hybridization. Appl. Environ. Microbiol. 46:636–641; Moseley, S. L., I. Huq, A. R. M. A. Alim, M. So, M. Samadpour-Motalebi, and S. Falkow. 1980. Detection of enterotoxigenic *Escherichia coli* by DNA hybridization. J. Infect. Dis. 142:892–898; Palva, A. M. 1983. ompA gene in the detection of *Escherichia coli* and other Enterobacteriaceae by nucleic acid sandwich hybridization. J. Clin. Microbiol. 18:92–100; Patamaroj, U., J. Seriwatana, and P. Echeverria. 1983. Identification of enterotoxigenic *Escherichia coli* isolated from swine with diarrhea in Thailand by colony hybridization, using three enterotoxin gene probes. J. Clin. Microbiol. 18:1429–1431), Neisseriae (Totten, P. A., K. K. Holmes, H. H. Handsfield, J. S. Knapp, P. L. Perine, and S. Falkow. 1983. DNA hybridization technique for the detection of *Neisseria gonorrheae* in men with urethritis. J. Infect Dis. 148:462–471), *Legionella* species (Grimont, P. A. D., F. Grimont, N. Desplaces, and P. Tchen. 1985. DNA probe specific for *Legionella pneumophila*. J. Clin. Microbiol. 21:431–437), viruses (Hyypia, T., P. Stalhandske, R. Vainionpaa, and U. Pettersson. 1984. Detection of enteroviruses by spot hybridization. J. Clin. Microbiol. 19:436–438), and parasites (Wirth, D. F., and D. M. Pratt. 1982. Rapid Identification of *Leishmania* species by specific hybridization of kenetoplast DNA in cutaneous lesions. Proc. Natl. Acad. Sci. USA 79:6999–7003). DNA probes that detect two species of human colonic *Bacteroides*, *B. thetaiotaomicron* and *B. vulgatus*, have been described (Kuritza, A.P., and A. A. Salyers. 1985. Use of species-specific DNA hybridization probe for enumerating *Bacteroides vulgatus* in human feces. Appl. Environ. Microbiol. 50:958–964; Salyers, A. A., S. P. Lynn and J. F. Gardner. 1983. Use of randomly cloned DNA fragments for identification of *Bacteroides thetaiotaomicron*. J. Bacteriol. 154:287–293), but no DNA probes have been reported for *B. fragilis* and other clinically significant anaerobes.

Since so many species of gram-negative anaerobes can cause infections in humans, a battery of species-specific DNA probes for identification of every species would be less useful than a smaller number of DNA probes that identify clinically important groups. Accordingly, objects of the invention are to obtain (i) a species-specific DNA probe for *B. fragilis*, (ii) a DNA probe that detects all species of the *B. fragilis* group, and (iii) a DNA probe that detects both *Bacteroides* and *Fusobacterium* species. The rationale for this grouping is that whereas all members of *Bacteroides-Fusobacterium* are resistant to aminoglycosides, *Fusobacterium* and oral *Bacteroides* organisms are generally susceptible to penicillins and cephalosposins. By contrast, resistance to beta-lactam antibiotics and to tetracycline is widespread among the members of the *B. fragilis* group, and special antibiotics such as clindamycin, cefoxitin, or metronidazole must often be used to treat infections due to these organisms (Finegold, S. M., supra).

Several patents have issued which relate to DNA probes or related technology for analysis of microorganisms (i.e., U.S. Pat. Nos. 3,930,956; 4,038,193; 4,358,538; 4,563,419; 4,581,333).

The invention herein described relates to the development DNA compositions of matter which are probes for detection of certain *Bacteroides* species which are responsible for a variety of human clinical infections. Such obligately anaerobic bacteria are notably difficult to cultivate and identify by conventional techniques. DNA hybridization probes have been developed which identify *Bacteroides fragilis* (i.e., pBFII-4), members of the *Bacteroides fragilis* group of species (i.e., pBE-3), and members of both *Bacteroides* and *Fusobacterium* species (i.e., pBO-21). The DNA hybridization probes described herein can be used to detect these bacteria in clinical specimens.

MATERIALS AND METHODS

Bacterial strains and culture conditions. The organisms used to screen potential DNA probes are listed in Table 1. Strains of *B. oralis, B. asaccharolyticus, B. melaninogenicus, F. necrophorum, F. nucleatum, Escherichia coli, Serratia marcescens, Pseudomonas aeruginosa, Proteus vulgaris, Klebsiella pneumoniae,* and *Enterobacter aerogenes* were obtained from the American Type Culture Collection, Rockville, Md. *B. melaninogenicus* BH was obtained from Burnham Hospital, Champaign, Ill. The *B. fragilis* group strains were obtained from the culture collection of the Virginia Polytechnic Institute Anaerobe Laboratory, Virginia Polytechnic Institute and State University, Blacksburg. This culture collection contains strains isolated in many different laboratories in different parts of the world (Johnson, J. L., supra). All *B. fragilis* group strains were those whose identification had been confirmed by DNA-DNA homology studies [Holdeman, L. V., and J. L. Johnson. 1982. Description of *Bacteroides loeschii* sp. nov. and emendation of the descriptions of *Bacteroides melaninogenicus* (Oliver and Wherry) Roy and Kelly 1939 and *Bacteroides denticola* Shah and Collins 1981. Int. J. Syst. Bacteriol. 32:399–409; Johnson, J. L., supra]. We used these strains rather than clinical isolates which had only been classified on the basis of biochemical tests because careful taxonomic studies have shown that this type of identification is not always reliable (Johnson, J. L., supra). All of the *B. fragilis* strains, *B. thetaiotaomicron* 0683-1, *B. melaninogenicus* 2381 and BH, *B. oralis* D27-824, and *B asaccharolyticus* 4188, were human clinical isolates. *B. vulgatus* 4025 was isolated from chicken meat. All other *Bacteroides* sp. strains were isolated from human feces or colon contents (Johnson, J. L., supra). Stocks of all strains were maintained at room temperature in prereduced chopped-meat broths (Carr Scarborough Microbiologicals, Inc.). For most experiments, the strains were grown at 37° C. in a Trypticase (BBL Microbiology Systems)-yeast extract-glucose medium (Holdeman, L. V., supra) under an atmosphere of nitrogen-carbon dioxide (80%/20%).

TABLE 1

| Bacterial species | Bacterial strains Strain no. |
|---|---|
| *B. fragilis* group | |
| *B. fragilis* type I[b] | 2553, type strain (ATCC 25285) |
| | 0479 |
| | 1552 |
| | 1582 |
| | 2044 |
| | 2556-1 |
| | 3277 |
| | 4361 |
| | 4509-B |
| | 4517 |
| | 29765 |
| *B. fragilis* type II[b] | 2393 |
| | 2552 |
| | 3392 |
| | 4076 |
| | 4117 |
| | 4225 |
| *B. vulgatus* | 4245 (ATCC 8482) |
| | 4025 |
| *B. thetaiotaomicron* | 5482 (ATCC 29148) |
| | 0633-1 |
| | 0940-1 |
| *B. ovatus* | 0038 (ATCC 8483) |
| | 0435 |
| *B. uniformis* | 0061 (ATCC 8492) |
| | 0909 |
| *B. distasonis* | 4243 (ATCC 8503) |
| | S6A-56 |
| Bacteroides sp. strain B5-21[c] | B5-21 |
| Bacteriodes sp. strain 3452-A[d] | 3452-A |
| | 2308 |
| *B. eggerthii* | B8-51 |
| Oral *Bacteroides* species | |
| *B. melaninogenicus* | 2381 (ATCC 25845) |
| | BH (Burnham Hospital isolate) |
| *B. asaccharolyticus* | 4188 (ATCC 25260) |
| *B. oralis* | D27-824 (ATCC 33269) |
| *Fusobacterium* species | |
| *F. necrophorum* | 2891 (ATCC 25286) |
| *F. nucleatum* | 4355 (ATCC 25586) |
| Other gram-negative bacteria | |
| *Escherichia coli* | ATCC 25922 |
| *Serratia maraescens* | ATCC 8100 |
| *Psuedomonas aeruginosa* | ATCC 27853 |
| *Proteus vulgaris* | ATCC 13315 |
| *Klebsiella pneumoniae* | ATCC 13883 |
| *Enterobacter aerogenes* | ATCC 13048 |

[b]L mess noted otherwise all strain numbers are Virginia Possennia institute designations.
[b]*B. fragilis* strains have been assigned to two types, based on DNA homology studies (13).
[c]Formerly *B. fragilis* subsp. a(13).
[d]An unnamed species, formerly belonging to *B. fragilis* subsp. disclose (13).

Construction of DNA probes. The DNA probes specific for *B. fragilis* were constructed by cloning random HindIII fragments of chromosomal DNA from *B. fragilis* strains 2553(type I) and 2393 (type II) into the *E. coli* plasmid pBR322, as previously described (Salyers, A. A. et al., supra). The DNA probe used to detect all members of the *B. fragilis* group and the probe used to detect all *Bacteroides* species were constructed similarly, using chromosomal DNA from *B. eqgerthii* B8-51 and *B. ovatus* 0038, respectively. HindIII chromosomal DNA fragments from other *Bacteroides* species were also screened but did not have the desired specificity. The specificity of the cloned chromosomal fragments was determined by the filtration and hybridization method outlined below. For hybridization experiments, recombinant plasmids were labeled with $\alpha$-$^{32}$P]deoxy-CTP (Amersham Corp.), using standard nick translation procedures (Maniatis, T., E. F. Fritsch, and J. Sambrook. 1982. Molecular cloning: a laboratory manual. Cold Spring Harbor Laboratory. Cold Spring Harbor, N.Y.). The specific activity of $^{32}$P-labeled plasmids was generally $10^7$ to $10^8$ cpm/μg of DNA. In some experiments, the recombinant plasmids were labeled with biotin, using a DNA detection kit (Bethesda Research Laboratories).

Buffers and reagents for filtering, prehybridization, and hybridization. Filtration of the disrupted bacterial cultures (see below) was performed with 10X standard saline-citrate (SSC), where 1X SSC is 0.15M NaCl plus 15 mM sodium citrate, ph 7.0. The prehybridization buffer (Maniatis, T. et al., supra) contained 6X SSPE, 5X BFP, 1% (wt/vol) glycine, 50% (vol/vol) formamide, and 100 μg of denatured, sonicated salmon sperm DNA per ml, where 20X SSPE is 3.6M NaCl-0.2M NaH$_2$PO$_4$-0.16M NaOH-20 mM Na$_2$ EDTA, pH 7.0, and 100X BFP is 2% (wt/vol) bovine serum albumin, 2% (wt/vol) Ficoll, and 2% (wt/vol) polyvinyl pyrrolidone. The hybridization solution (Maniatis, T. et al., supra) contained 5X SSPE, 1X BFP, 50% (vol/vol) formamide, 100 μg of salmon sperm DNA per ml, 0.3% (wt/vol) sodium dodecyl sulfate (SDS), and 10% (wt/vol) dextran sulfate. After hybridization, filters were washed once in 2X SSPE-0.2% (wt/vol) SDS and twice in 0.2X SSPE-0.2% SDS. These same reagents were used in experiments that used biotin-labeled DNA probes, except where indicated otherwise in the Bethesda Research Laboratories detection kit instructions.

Determining the specificity of the DNA probes. Recombinant plasmids, containing the randomly cloned *Bacteroides* sp. DNA fragments, were labeled with $^{32}$P and screened for specificity against the strains listed in Table 1. Cultures were grown to a density of approximately $10^9$ cells per ml. Bacteria (5.0 ml) were harvested by centrifugation (16,000×g, 15 min, 4° C.) and suspended in 5.0 ml of distilled water. Sodium hydroxide was added to a final concentration of 0.5N, and the cell suspension was heated to 90° C. for 20 to 30 min. This treatment lyses cells and denatures chromosomal DNA. The lysed cell suspension was neutralized with 0.5N HCl (1.25 ml of 2.5N HCl), diluted 1:1 by adding 7.5 ml of 20X SSC (final concentration, 10X SSC), and chilled on ice for 15 to 20 min. Portions of the neutralized suspension (generally in the range of 0.05 to 0.5 ml, brought to a constant final volume of 4.0 ml with 10X SSC) were filtered onto prewetted spots (prewetted with 10X SSC) of a strip of nitrocellulose paper (type HAWP, 0.45 μm; Millipore Corp.) by vaccum aspiration. The spots (2.5-cm diameter) were rinsed with 4.0 ml of 0X SSC. The filters were allowed to air dry and then heated to 85° C. (at least 3 h in a vacuum oven or at least 6 h in a conventional oven) to fix DNA to the nitrocellulose. After heating, the filters were incubated with prehybridization buffer for 2 to 3 h at 42° C. in sealable plastic bags. The prehybridization buffer was then extruded and replaced with hybridization buffer containing approximately $10^6$ cpm of $^{32}$P-labeled plasmid probe. Hybridization was allowed to proceed for up to 12 h at 42° C. Filters were then washed once in 2X SSPE-0.2% SDS to remove nonspecifically bound probe. Each wash lasted 20 to 25 min at 60° C. Filters were dried for 1 to 2 h at 60° to 70° C. to remove excess moisture, and hybridization of the $^{32}$P-labeled plasmid probes to bacterial DNA on the nitrocellulose strips was detected by either liquid scintillation counting or autoradiography. For liquid scintillation counting, filters were cut up into squares, placed into scintillation vials, and counted in ACS scintillant (Amersham Corp.). For autoradiography, exposure times of 12 to 24 h were generally adequate to detect hybridization. In experiments with biotin-labeled probes, the manufacturer's instructions were followed.

Liquid scintillation counting was used in the initial experiments to screen the specificity of the constructed DNA probes. A probe was considered specific for *B. fragilis* if (i) the amount of $^{32}$P-labeled probe (counts per minute) that hybridized to filters containing DNA from $10^7$ to $10^8$ *B. fragilis* cells was directly proportional to the amount of *B. fragilis* DNA on the filters, and (ii) the amount of $^{32}$P-labeled probe that hybridized to filters that contained DNA from $10^7$ to $10^8$ cells of other species was <10 to 15% of that which hybridized to a comparable amount of *B. fragilis* DNA. Similar criteria were used to define type-specific, group-specific, and genus-specific probes.

Blood culture experiments. Whole rabbit blood was seeded with a pure culture of *B. fragilis* to a final concentration of about $10^2$ bacteria per ml. The blood was then inoculated on a 10% (vol/vol) basis into anaerobic brain heart infusion blood culture bottles (GIBCO Laboratories), and incubated at 37° C. At timed intervals (usually 6 h, for up to 72 h), a 5.0-ml sample was aseptically removed from the blood culture and centrifuged (16,000×g, 15 min, 4° C.) to pellet bacteria. Cells were suspended in 5.0 ml of distilled water, lysed with NaOH, and filtered. Filters were then incubated with a *B. fragilis*-specific $^{32}$P-labeled probe as described above.

All novel DNA hybridization probes of the invention mentioned by plasmid number for detection of *Bacteroides fragilis*, members of the *Bacteroides fragilis* group of species, and members of both *Bacteroides* and *Fusobacterium* species are maintained in a permanent culture collection of the University of Illinois at Urbana-Champaign in the laboratory of Dr. Abigail A. Salyers in the Department of Microbiology, 131 Burrill Hall, 407 South Goodwin Avenue, Urbana, Ill. 61801. Access to these deposits is available to the U.S. Patent and Trademark Office during the pendency of this application. In the event a patent shall be granted on the invention described herein, all restrictions, if any, on the availability to the public of these deposits will be removed.

RESULTS

The following examples of results further serve to illustrate the invention and are not intended to be limitative thereof.

Specificity of DNA probes. The results of a typical screening experiment are given in Table 2. Based on these and similar data for other DNA probes, we identified three probes (pBFII-4, pBFII-5, and BFII-6) that hybridized with all *B. fragilis* strains tested (Table 3). These three probes detected both *B. fragilis* DNA homology subgroups (types I and II). Some of the clones we screened were specific for type I or type II (Table 3). We also found one probe (pBE-3) that hybridized with all *B. fragilis* group species tested and one probe (pBO-21) that hybridized with DNA from all *Bacteroides* species, with DNA from *F. necrophorum*, and with DNA from *F. nucleatum*.

TABLE 2

Hybridization of the *B. fragilis* specific probe pBF11-5 with DNA from the strains listed in Table 1

| Organism | Amt of $^{32}$P-labeled pBF11-5 bound (cpm)[a] to samples containing: | | | |
|---|---|---|---|---|
|  | $5 \times 10^6$ cells | $1 \times 10^7$ cells | $3 \times 10^7$ cells | $5 \times 10^7$ cells |
| *B. fragilis* | | | | |
| 2553 (type I) | 117 | 472 | 1.394 | 2.419 |
| 2393 (type II) | 98 | 497 | 1.437 | 2.298 |
| Other *B. fragilis* group spp.[b] | 42–74 (58) | 59–79 (69) | 60–82 (71) | 65–98 (81) |
| Other Bacteroides spp.[d] | 49–69 (59) | 52–74 (63) | 64–88 (76) | 69–96 (82) |
| Fusobacterium spp.[e] | 56–62 (59) | 61–65 (63) | 65–73 (69) | 77–87 (82) |
| Enteric bacteria Pseudomonas sp.[f] | 58–75 (66) | 60–80 (70) | 65–84 (75) | 79–100 (89) |

[a] Values reported are averages of at least triplicate determinations. Background determined as the counts bound to nitrocellulose through which only media has been filtered, reanged from 50 to 80 cpm. Background has not been subtracted from values shown.
[b] *B. thetaiotaomicron, B. uniformis, B. distasonics,* Bacteroides sp. strain 3452-A.*B. ovatus, B. vulgatus* and *B. eggerthii.*
[c] Indicated are range of values and averages (in parentheses) obtained for the various species.
[d] *B. melaninogenicus, B. asaccharolyticus,* and *B. oralis.*
[e] *F. nucleatum* and *F. necrophorum.*
[f] *Escherichia coli, Serratia marcescens, Proteus vulgaris, Klebsiella pneumoniae, Enterobacter aerogenes,* and *Pseudomonas aeruginosa.*

TABLE 3

Summary of Bacteroides sp. DNA probes

| Probe | Derived from: | Approximate size of cloned DNA fragment (kb) | Specific for: |
|---|---|---|---|
| pBFII-4 | *B. fragilis* 2393 (type II) | 1.6 | *B. fragilis* |
| pBFII-5 | *B. fragilis* 2393 (type II) | 1.8 | *B. fragilis* |
| pBFII-6 | *B. fragilis* 2393 (type II) | 2.2 | *B. fragilis* |
| pBFI-67 | *B. fragilis* 2553 (type I) | 1.5 | *B. fragilis* type I only |
| pBFI-68 | *B. fragilis* 2553 (type I) | 2.8 | *B. fragilis* type I only |
| pBFI-70 | *B. fragilis* 2553 (type I) | 5.0 | *B. fragilis* type I only |
| pBFII-7 | *B. fragilis* 2393 (type II) | 1.4 | *B. fragilis* type II only |
| pBFII-8 | *B. fragilis* 2393 (type II) | 2.4 | *B. fragilis* type II only |
| pBE-3 | *B. eggerthii* B8-51 | 0.6 | All *B. fragilis* group strains |
| pBO-21 | *B. ovatus* 0038 | 0.9 | All Bacteroides sp. strains. *F. nucleatum. F. necrophorum* |

Figure 1B:
Figure 1C:
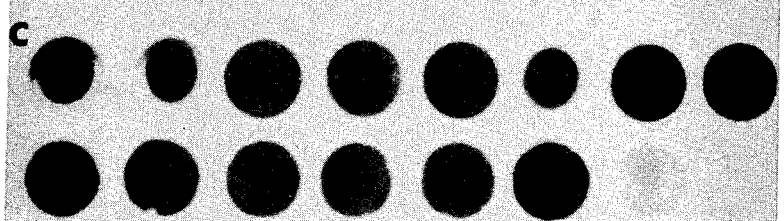

Detection of hybridized DNA probes. Liquid scintillation counting was used to detect hybridization in these initial screening experiments because it provided a quantitative measure of the differences between positive and negative results (cf. Table 2). These differences were also readily detectable by autoradiography (FIG. 1). In general, each of the probes listed in Table 3 had a similar affinity for different strains of the species or group for which it was specific (data not shown).

FIG. 1. Use of autoradiography to detect specific hybridization of the *B. fragilis* $^{32}$P-labeled probe pBFII-5 (filter A), the *B. fragilis* group $^{32}$P-labeled probe pBE-3 (filter B), or the *Bacteroides-Fusobacterium* $^{32}$P-labeled probe pBO21 (filter C) to nitrocellulose filters containing DNA from various gram-negative bacteria. Each filter spot contained ca. $10^8$ disrupted bacteria. Filter A contained: (row 1, from left) *B. fragilis* type I strains 2553, 0479, and 1552, *B. fragilis* type II strains 2393, 2552, and 3392, no cells; (row 2) *B. thetaiotaomicron, B. distasonis, B. ovatus, B. melaninogenicus, F. necrophorum, E. coli,* no cells. Filters B and C contained: (row 1) *B. fragilis* type I 2553, *B. fragilis* type ii 2393, *B. vulgatus, B. thetaiotaomicron, B. uniformis, B. ovatus, B. distasonis,* Bacteroides sp. strain B5-21; (row 2) *Bacteroides* sp. strain 3452-A, *B. eggertinii, B. melaninogenicus, B. asaccharolyticus, F. necrophorum, F. nucleatum, E. coli,* no cells.

We also tried to detect *Bacteroides* species by using biotin-labeled DNA probes rather than $^{32}$P-labeled probes. In this system, peroxidase-labeled avidin or streptavidin is used to detect hybridized biotinylated DNA. However, some component in the *Bacteroides* sp. lysed cell suspensions reacted directly with the streptavidin-conjugated enzyme so that color developed nonspecifically on nitrocellulose filters which contained DNA that had not been hybridized with the DNA probe. We attempted to eliminate this nonspecific color (i) by extracting the lysed cell suspensions with phenol-chloroform and ethyl ether prior to filtration, (ii) by treating filters after filtration with proteases, or (iii) by washing filters (after filtration) with ethanol (10 to 75%), formamide (25 to 75%), acetic anhydride (0.25 to 1.0%), triethanolamine (0.1 to 1.0M), NaOH (0.2 to 1.0M), ammonium hydroxide (0.1 to 1.0M), sodium iodide (saturated solution), SDS (0.1 to 1%), or peroxide (1 to 10%). All attempts were unsuccessful. Consequently, we used $^{32}$P-labeled probes in all subsequent experiments.

Identity of pBO-21. Because of the broad specificity of pBO-21 and pBE-3 (cf. FIG. 1), we wanted to determine whether the cloned *Bacteroides* sp. DNA fragments that were carried by these two probes might code for rRNA. Paster et al. (Paster, B. J. et al., supra) have reported that 16SrRNA sequences are highly conserved among human *Bacteroides* species, are similar to those of some *Fusobacterium* spp., and are distinct from those of most other bacteria. Recently, a *Bacteroides* sp. 16S rRNA gene has been cloned (Weisburg, W. G., Y. Oyaizo, H. Oyaizu, and C. R. Woese. 1985. A natural relationship between bacteroides and flavobacteria. J. Bacteriol. 164:230–236). This clone, M13mp8BF1, was used to test pB021 and pBE-3 for cross-hybridization with 16S rRNA sequences. Results of Southern blot analyses (FIG. 2) indicated that the cloned 0.9-kilobase DNA fragme in pBO-21 hybridized to M13mp8BF1. However, the cloned 0.6-kilobase DNA fragment in pBE-3 did not hybridize with the cloned 16S rRNA gene.

Figures 2A, 2B:
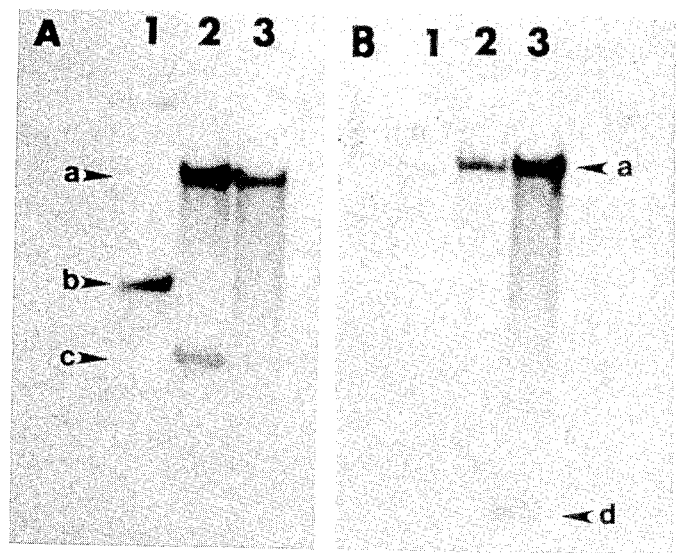

FIG. 2. Hybridization of $^{32}$p-labeled pBO-21 (A) of pBE-3 (B) to Southern blots containing HindIII digests of: lane 1, M13mp8-pBF1a recombinant plasmid that carries the gene coding for 16S rRNA of *Bacteroides* spp. (23):lane 2, pBO-21:lane 3, pBE-3. Arrows indicate (a) the vector pBR322, (b) the segment of M13mp8 that carries the gene coding for *Bacteroides* sp. 16S rRNA, (c) the cloned DNA fragment in pBO-21 and (d) the cloned DNA fragment in P.

Sensitivity of detection. Hybridization of $\alpha$-$^{32}$P-labeled probe to *Bacteroides* sp. DNA on nitrocellulose was first detectable by liquid scintillation counting when approximately $10^7$ lysed bacteria had been filtered, and the amount of hybridization increased linearly with the number of bacteria in the sample until approximately $10^8$ bacteria had been filtered. Hybridization of a $^{32}$P-labeled probe to the DNA from $10^7$ to $10^8$ *Bacteroides* sp. cells was also readily detectable by autoradiography (exposure time of 12 to 24 h). It was possible to detect lower concentrations of bacteria (ca. $10^6$) by autoradiography, but this required longer exposure time (at least 36 h).

Detecting *B. fragilis* in mixed cultures. In some cases, it might be possible to use DNA probes to detect *Bacteroides* spp. directly in a clinical specimen. However, *Bacteroides* sp. infections are frequently polymicrobic. To determine whether our DNA probes could be used to detect *Bacteroides* species in mixtures which contained other organisms, we mixed pure cultures of *B. fragilis* 2553 with *E. coli* in various proportions before lysing the bacteria and carrying out the hybridization procedure. We could detect *B. fragilis* with pBFII-4 even if it comprised as little as 10% of the cells in the mixture. Similar results were obtained when *B. fragilis* 2553 (type I) was mixed with *B. fragilis* type II or with other species of *Bacteroides*, enteric bacteria, or *Fusobacterium* and probed with the type I-specific probe pBFI-67 (Table 4).

TABLE 4

Detection of *B. fragilis* in mixed culture. using pBFI-67

| *B. fragilis* 2553 type I (bacteria per ml) | Other bacteria (bacteria per ml) | Amt of $^{32}$P-labeled pBFI-67 bound (cpm)[a] |
|---|---|---|
| $10^7$ | None | 512 |
| $10^7$ | *B. fragilis* type II 2393 ($10^8$) | 496 |
| $10^7$ | *B. thetaioiaomicron* 5482 ($10^8$) | 502 |
| $10^7$ | *F. necrophorum* 2891 ($10^8$) | 487 |
| $10^7$ | *E. coli* 25922 ($10^8$) | 499 |
| None | *E. coli* 25922 ($10^8$) | 46 |
| None | *E. coli* K-12(pBR322) ($10^7$) | 7.439 |

[a]Values represent averages of triplicate determinations. Background generally 50 to 80 cpm. has not been subtracted from values shown.

All of our *Bacteroides* sp. probes have been constructed by cloning *Bacteroides* sp. DNA segments in pBR322 Although it is not a naturally occurring plasmid, pBR322 has been derived from plasmids that are native to the *Enterobacteriaceae* (i.e., ColEl plasmids). Thus, our probes might hybridize with homologous sequences carried by enteric bacteria in a specimen. The reaction of our DNA probes with a strain of *E. coli* that carries pBR322 is shown in Table 4. To date, we have been seen any evidence that $^{32}$P-labeled pBR322 cross-hybridizes with *Bacteroides* sp. DNA (Kuritza, A. P. et al., supra; Salyers, A. A. et al., supra).

Blood cultures. Anaerobic bacteria such as *Bacteroides* spp. have been associated with bacteremia (Allen, S. D. et al., supra). Although the concentration of bacteria usually found in blood is too low to be detected directly by the DNA hybridization method used in this study (Reller, L. B., P. R. Murray, and J. D. MacLowry 1982. Cumitech 1A. Blood cultures II. Coordinating ed., J. A. Washington II. American Society for Microbiology, Washington, D.C.), it should be possible to use DNA probes to detect bacteria which have been grown in blood culture medium. To test this, we seeded whole rabbit blood with a pure culture of *B. fragilis* ($10^2$ per ml) and used it to inoculate. Under these conditions, *B. fragilis* was generally detectable within 24 to 36 h after the blood culture bottle had been inoculated. Typical results are shown in FIG 3.

Figure 3:
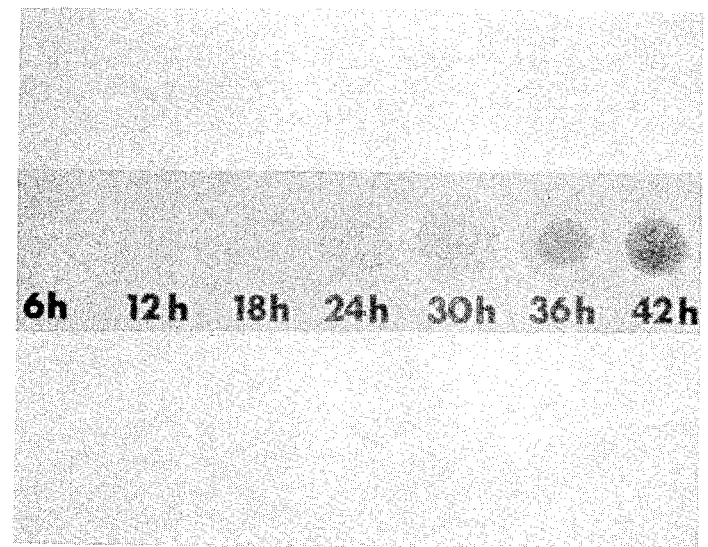

FIG. 3. See the use of $^{32}$P-labeled pBFII-5 to detect *B. fragilis* 2553 in blood cultures. A pure culture of *B. fragilis* was mixed with whole rabbit blood and then inoculated into anaerobic brain near infusion broth (see text). At timed intervals, samples were removed and probed with $^{32}$P-labeled pBFII-5. Thus, components of the whole blood or the blood culture medium did not interfere with detection of *B. fragilis* by DNA hybridization.

DISCUSSION

The detection and identification of bacteria by nucleic acid hybridization offers two major advantages over conventional bacteriological procedures, particularly for organisms such as anaerobic bacteria which are difficult to cultivate and identify. First, DNA probes identify an organism at the genetic level. Although the gram-negative anaerobes, which account for the majority of anaerobic clinical isolates, represent a heterogeneous group of species, some of them are phenotypically quite similar. This means that many different tests must be done to obtain a species identification. In addition, some species are poorly defined or are not readily differentiated on the basis of biochemical tests (Holdeman, L. V. et al., supra; Johnson, J. L., supra). Three of our probes, taken together, appear to subdivide the gram-negative anaerobes into three convenient groups. pBFII-4 (or pBFII-5 or pBFII-6) identifies *B. fragilis*, the most commonly isolated anaerobic pathogen. pBE-3 hybridizes with all members of the *B. fragilis* group. An isolate that does not react with pBFII-4 but reacts with pBE-3 is probably a member of one of the colonic *Bacteroides* species other than *B. fragilis*. pBO-21 detects *Bacteroides* and *Fusobacterium* species. Thus, an isolate that does not react with either pBFII-4 or pBE-3 but reacts with pBO-21 may be an oral *Bacteroides* or a *Fusobacterium* species.

A second advantage of DNA hybridization probes is that it may be possible in some cases to detect organisms directly in a specimen or after a preliminary enrichment step such as growth in a blood culture bottle. This would eliminate the time and special equipment required for cultivation of *Bacteroides* species. Moreover, frozen specimens could be used. We have shown that our DNA probes can detect *Bacteroides* species in a mixture that contains other organisms or in blood culture medium. One problem with using DNA probes directly on a specimen is that the organism of interest may be present in too low a concentration. We found that the concentration of *Bacteroides* species had to be at least $10^6$ per ml and that in a mixed culture *Bacteroides* species had to account for at least 10% of the mixture. If these conditions are not fulfilled, a false-negative result would be obtained. A second problem is the cross-reactivity of our probes with pBR322 sequences. It is unlikely that *Bacteroides* sp. DNA will cross-react with these sequences because *Bacteroides* are so distant genetically from other gram-negative bacteria (Paster, B. J. et al., supra; Weisburg, W. G. et al., supra). However, a facultative bacterium which carried some of these sequences could give a false-positive reaction. This problem could be circumvented by using the cloned insert alone as the hybridization probe. Alternatively labeled pBR322 (no insert) could be included together with pBFII-4, pBE-3, and pBO-21 in any screening procedure. A specimen which contained DNA that cross-hybridized with the pBR322 control would have to be analyzed by alternative means, e.g., by first obtaining isolated colonies.

The purpose of this invention was to identify DNA probes that might be useful for identification of clinical gram-negative anaerobes. Since the fermentation tests used in conventional identification procedures are not always reliable (i.e., results are not always in agreement with DNA-DNA homology studies), it is essential to use strains whose identification has been confirmed by DNA-DNA homology experiments for the initial screening of potential DNA probes. The problem is with this is that only a limited number of such strains are available. To establish the utility of DNA probes such as those described in this report, it will be necessary not only to screen a number of recent clinical isolates, but also to determine whether any disagreements that arise between results of the DNA probe test and results of identification by conventional techniques are due to incorrect specificity of the DNA probe or to the failure of conventional tests to provide a correct identification.

The approach described herein to obtaining specific DNA probes, which is similar to that described by Fitts et al. (Fitts, R. M. et al., supra), differs from those reported previously for clinical applications in that we cloned individual random fragments of chromosomal DNA rather than using whole chromosomal DNA (Hodgson, A. L. M., and W. P. Roberts. 1983. DNA colony hybridization to identify Rhizobium strains. J. Gen. Microbiol. 129:207-212), a fraction of chromosomal DNA (Grimont, P. A. D. et al., supra), cloned genes (Moseley, S. L. et al., supra; Palva, A. M., supra; Patamaroj, U. et al., supra), or plasmids (Hills, W. E. et al., supra; Totten, P. A. et al., supra). Our approach has the advantage that the cloned fragments, once obtained, provide a reproducible source of the DNA probe. Also, this approach can be used with organisms for which little genetic information is available or which do not have plasmids that are diagnostic for a species or group. Using cloned chromosomal fragments has the disadvantage that probes that detect regions of the chromosome are not as sensitive as probes that detect multicopy plasmids or rRNA. The most sensitive probes will be those that detect sequences or rRNA, but it may be difficult to obtain probes containing rRNA genes that are specific for individual species because rRNA sequences tend to be highly conserved. The sensitivity of our probe pBO-21, which cross-reacted with a 16S rRNA gene from *Bacteroides*, appeared similar to that of the other probes. But the filtration procedure we use has been optimized for trapping bacterial DNA (Kuritza, A. P. et al., supra). Thus, it may be possible to obtain greater sensitivity with pBO-21 by using conditions that enhance the capture of bacterial rRNA on the nitrocellulose filters.

A major limitation of our approach is that this method currently requires the use of radiosotopes. Not only does this create safety and disposal problems, but $^{32}$P-labeled probes are short-lived. Methods for labeling probes with biotin instead of radiosotopes have recently become commercially available. In our experience, however, probes labeled with biotinylated nucleotides gave nonspecific positive reactions. Other investigators have reported similar results (P. Zwadyk, R. C. Cooksey, and C. Thornsberry, Abstr, Annu. Meet. Am. Soc. Microbiol, 1985, C334, p, 355). As other methods for nonisotopically labeling nucleic acid probes become available, the use of these probes to detect organisms in a clinical setting should become more feasible.

What is claimed is:

1. A composition of matter for detecting the presence of *Bacteroides fragilis* by hybridization to DNA from said organism comprising the DNA probe pBFII-4 in combination with an acceptable carrier.

2. A composition of matter for detecting the presence of the *Bacteroides fragilis* group of species by hybridization to DNA from said organisms comprising the DNA probe pBE-3 in combination with an acceptable carrier.

3. A composition of matter for detecting the presence of *Bacteroides* sp. strains and *Fusobacterium* sp. strains by hybridization to DNA from said organisms comprising the DNA probe pBO-21 in combination with an acceptable carrier.

4. A DNA probe according to claim 2 wherein said probe hybridizes with DNA from *B. fragilis* type I, *B. fragilis* type II, *B. vulgatus*, *B. thetaiotaomicron*, *B. ovatus*, *B. uniformis*, *B. distasonis*, *Bacteroides* sp. strain B5-21, *Bacteroides* sp. strain 3452-A, and *B. eggerthii*.

5. A DNA probe according to claim 3 wherein said probe hybridizes with DNA from *B. fragilis* type I, *B. fragilis* type II, *B. vulgatus*, *B. thetaiomicron*, *B. ovatus*, *B. uniformis*, *B. distasonis*, *Bacteroides* sp. strain B5-21, *Bacteroides* sp. strain 3452-A, *B. eggerthii*, *B. melaninogenicus*, *B. asaccharolyticus*, *B. oralis*, *Fusobacterium necrophorum*, and *F. nucleatum*.

* * * * *